United States Patent
Hogan

(10) Patent No.: US 6,401,071 B1
(45) Date of Patent: Jun. 4, 2002

(54) SYSTEM AND METHOD FOR AUTOMATICALLY RECORDING ANIMAL INJECTION INFORMATION

(75) Inventor: Thomas Hogan, Marietta, GA (US)

(73) Assignee: Agecom, Inc., Marietta, GA (US)

( * ) Notice: Subject to any disclaimer, the term of this patent is extended or adjusted under 35 U.S.C. 154(b) by 0 days.

(21) Appl. No.: 09/477,262

(22) Filed: Jan. 4, 2000

(51) Int. Cl.[7] .............................................. G06F 17/60
(52) U.S. Cl. .................... 705/2; 340/573.1; 340/573.3; 340/572.1; 340/575.8
(58) Field of Search .......................... 340/573.3, 573.1, 340/572.1, 572.8, 825.06, 286.07; 705/2; 604/890.1, 891, 407

(56) References Cited

U.S. PATENT DOCUMENTS

| | | | | |
|---|---|---|---|---|
| 5,251,647 | A | * 10/1993 | Velten | 128/899 |
| 5,288,291 | A | * 2/1994 | Teoh | 604/60 |
| 5,790,047 | A | * 8/1998 | Golan | 340/825.54 |
| 5,882,338 | A | * 3/1999 | Gray | 604/131 |
| 6,236,318 | B1 | * 5/2001 | Yang et al. | 340/573.3 |
| 6,270,455 | B1 | * 8/2001 | Brown | 600/300 |
| 6,271,757 | B1 | * 8/2001 | Touchton et al. | 340/573.1 |

FOREIGN PATENT DOCUMENTS

| | | | | |
|---|---|---|---|---|
| WO | WO 93/09837 | * | 5/1993 | A61M/29/00 |

OTHER PUBLICATIONS

Betsy Freese, Aug. 1991, Livestock Syringes, Successful Farming, Iowa edition, vol. 89, Issue 8, p. 48.*

* cited by examiner

Primary Examiner—Tariq R. Hafiz
Assistant Examiner—Robert Morgan
(74) Attorney, Agent, or Firm—Troutman Sanders LLp; Wm. Brook Lafferty

(57) ABSTRACT

A system and method for automatic recordation of information relating to administration of medicines to animals are accomplished by a transmitting syringe simultaneously injecting and marking an animal while transmitting, responsive to actuation of the transmitting syringe, a first signal containing information relating to the actuation of the transmitting syringe and the resulting injection of the animal. An electronic identification device (EID) such as a bolus, ear tag or subcutaneous implant is attached to the animal and provides a unique electronic identification of the animal. A receiver receives both the first signal from the transmitting syringe and the electronic identification of the animal, as provided by the EID. Information contained in the respective signals is maintained in a computer database for review and analysis.

10 Claims, 3 Drawing Sheets

SYSTEM AND METHOD FOR AUTOMATICALLY RECORDING ANIMAL INJECTION INFORMATION

TECHNICAL FIELD

The present invention relates to systems and methods for automatically recording information relating to animal injections. More particularly, the present invention relates to a system and method for the combined, coordinated and automatic recordation of animal injection and identification information into a computer database.

BACKGROUND INFORMATION

The regular and accurate administration of medicine to animals such as hogs and cattle is critical to the physical health of the animals, the resulting quality of the food products the animals deliver, and the sense of confidence the consumer has in the wholesomeness of those food products. These concerns are equally prevalent in both the cattle and hog industries, so it will be understood and appreciated that the following references to cattle, made for illustrative simplicity, are equally applicable to hogs.

In cattle, vast numbers of different, complex medicinal regimens have been developed and implemented in an effort to generate healthier animals that produce a safe, higher quality and quantity of beef. Because slaughtered beef is valued, in significant part, on its quality characteristics, and because the premium paid for high quality beef is high, those raising cattle for profit remain in search of the optimum medical regimen. Furthermore, pharmaceutical companies almost blindly spend billions of dollars developing individual medicines without the opportunity or resources to conduct a large-scale, extended length individual animal-based field tests. Compounding the problem is the fact that current systems and methods of record keeping among cattle ranchers and pork producers fail to provide the kind and volume of high quantity, high integrity information about the effects of various medicines on individual animals that would alert pharmaceutical developers of the most likely avenues for future successful drug development. Additionally, the growing concerns by consumers over the residual effects of the application of these medical treatments (as they relate to food safety) are not satisfied by any present method or system for medical treatment tracking or accounting.

The life of a head of cattle, from calf to slaughter, is in the range of one to two years (the period is less for hogs). Even in this relatively short period of time, the numbers of medical treatments a particular animal may receive are numerous. Additionally, the numbers of head of cattle a cattleman must raise to be profitable is generally large. Even if a cattleman endeavors to be diligent in the recordation of medicines given to individual cattle in his herd, the logistics of keeping such records make the task nearly impossible. First, animals as big as cattle are generally unappreciative of being stuck with the rather large needles typically used to inject medicines. Outweighed by a factor of three, four or five, the cattleman faces a battle just to deliver the injection. In addition to the physical struggle of man vs. animal, the conditions in many feedlots can be brutally inhospitable, especially in colder months and in the less temperate regions where cattle are typically raised. Finally, many cattle operations operate on tight profit margins, making the cost of additional labor for recording and maintaining recorded data (which may or may not have a positive effect on the price of the end product) prohibitive. Given these impediments, it is nearly impossible for a cattleman to simultaneously and accurately record information relevant to medicines and the animals the medicines are given to.

Numerous advances in the medicine delivery systems have helped cattlemen gain increased control over the historically chaotic task of administering medicines to animals. Notably, U.S. Pat. No. 5,961,494, which is specifically incorporated herein by reference, the inventor of which is also the inventor herein, discloses a marking syringe which, when actuated, simultaneously injects medicine into an animal and places a mark on the skin of the animal in proximity to the location of the injection. This marking syringe (known commercially as the "VAC-MARC") cleverly reduces what was formerly a clumsy, two-step injecting and marking process into one step—the actuation of the syringe. Nonetheless, a cattleman using the marking syringe taught by the '494 patent and desiring to maintain records of injections would still have to somehow identify the animal and then manually record the fact that that particular animal had been injected.

Beyond the logistics of injecting and marking an animal, proper identification of the animal is also important. In this regard, it is well known to skilled cattlemen that an electronic identification device (EID) such as a bolus, ear tag, ear button or sub-cutaneous implant can be used to electronically identify animals such as cattle. One such boluses are well known in the industry and are produced by companies such as Allflex, USA, 2805 W. $12^{th}$ Street, Dallas, Tex. 75211-0270, (972) 456-3686, www.allflexusa.com; Y-Tex Corporation, P.O. Box 1450, Cody, Wyo. 82414, www.ytex.com; and MagTrac, 3203 Third Avenue North, Billings, Mont. 59101, (406) 252-6690. Boluses such as those available thorough these channels can be swallowed by the animal and will remain inside the animal for a period of time. The bolus, if active, transmits a signal which can be read by a hand-held bolus reader. If passive, the bolus can be triggered to transmit an identification signal by a trigger signal transmitted by another signal source. Once the trigger signal is recognized by the bolus, the bolus transmits a responsive identification signal. Although such a bolus system can be useful to identify an animal, no current system exists by which a bolus and bolus receiver can be used to assist in the automatic tracking of the administration of medicines to animals.

Accordingly, there is a need for a system and method in which information relating to the administration of medicines to animals can be automatically recorded. There is a further need for a system and method of combining and coordinating the automatic recordation of injection and other medicine administration data with the automatic recordation of animal identification data. A still further need exists for a system and method for accomplishing the aforementioned needs and reliably and automatically recording the resulting information in a location and format in which it can be later used in the improved development of animal food products such as beef.

BRIEF SUMMARY OF THE INVENTION

The present invention relates to a novel system for automatic recordation of information relating to administration of medicines to animals.

A preferred embodiment of the invention implements a transmitting syringe for simultaneously injecting and marking an animal while transmitting, responsive to actuation of the transmitting syringe, a first signal containing information relating to the actuation of the transmitting syringe and the resulting injection of the animal. Additionally, an electronic identification device (EID) such as a bolus is attached to the animal for providing a tamperresistant electronic identification of the animal. Additionally, a receiver is implemented to receive both the first signal from the transmitting syringe and the electronic identification of the animal, as provided by the EID.

After receipt of the respective signals by a receiver, the signals are maintained in a computer database for review and analysis.

DETAILED DESCRIPTION

Figure 1:
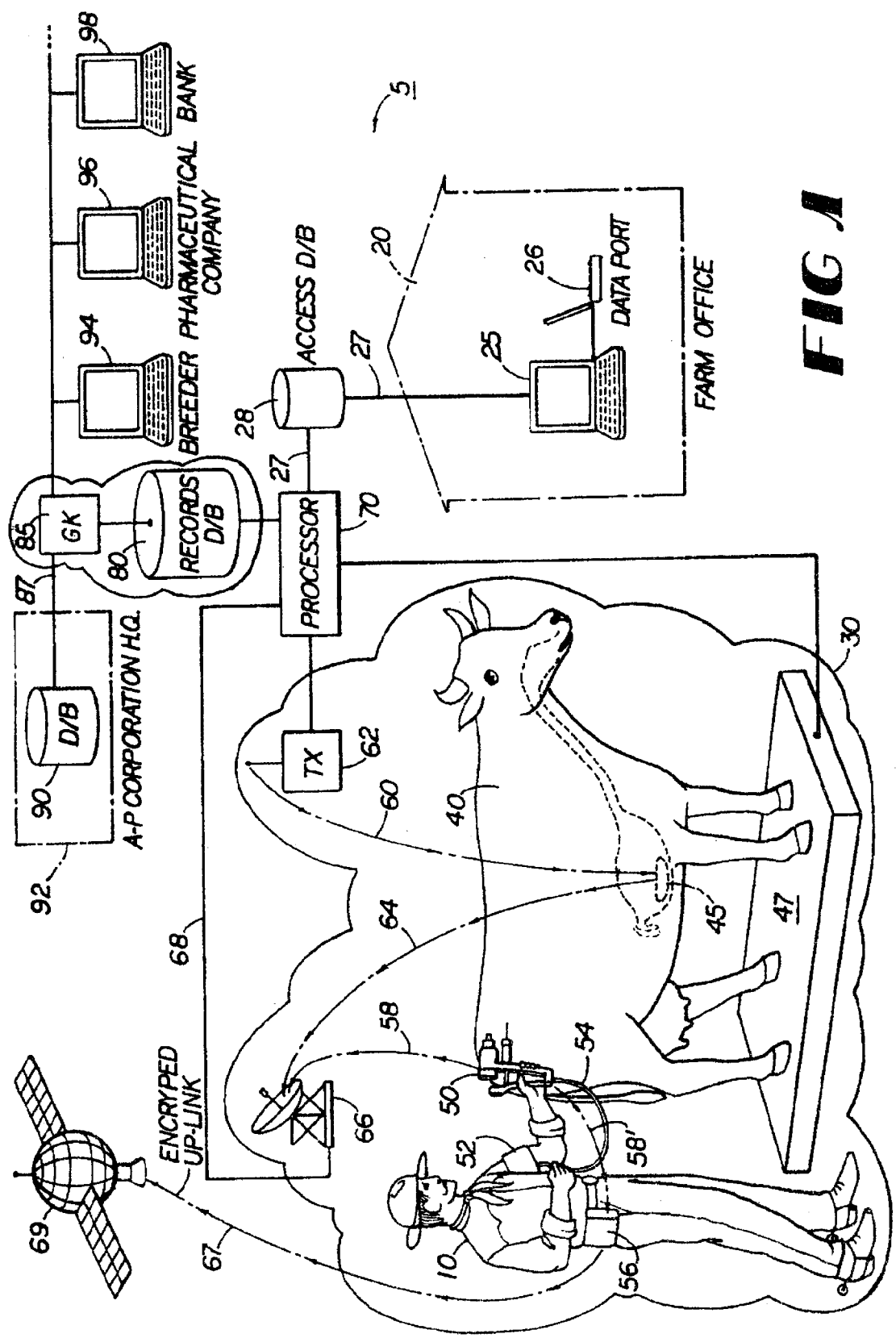
FIG. 1 depicts an exemplary embodiment of the present invention in an exemplary operating environment.

Referring now to the drawings, FIG. 1 depicts an exemplary embodiment of the present invention in an exemplary operating environment.

More specifically, the Automatic Injection Recordation System 5 (hereinafter referred to as the "System") features logistical and procedural devices by which a cattleman 10 can operate out of a farm office 20 in a particular remote injection area 30 to deliver injections to an animal 40 and, importantly, automatically record data (also referred to as "information") relating to the injections.

In operation, the cattleman 10 begins operation of the System 5 by entering identification data such as personal identification information into a personal computer ("PC") 25 in or near his farm office 20. Depending on the desires of the system administrators, different levels and types of information may be required of the cattleman 10 before the cattleman 10 is authorized for further use of the System 5. Determination as to authorization may be made by comparison of information requested of the cattleman 10 to information maintained in a database such as the access database 28. Information contained in the access database 28 relating to authorization criteria for cattlemen could originate from any of a wide variety of sources such as a system administrator, drug manufacturer, or the like.

As far as the specifics of authorization are concerned, it may be sufficient for the cattleman 10 to enter an indicator of his personal identity, such that verification as to his training relating to the System 5 can be verified. It is understood that a substantial aspect of the value of information derived from operation of the System 5 is the guarantee that the information is devoid of errors which may originate with operation by untrained or improperly trained cattlemen. Verification that a particular cattleman has training sufficient to operate the system properly and, therefore, produce reliable data is considered valuable. Beyond verification that a particular cattleman is properly trained for operation of the System 5, it may also be desirable to require the cattleman 10 to enter into the system, for authorization, the specific medical regimen about to be applied by the cattleman 10 to the animal 40. Clearly, if the cattleman 10 is not authorized, by virtue of a lack of training or certification, to deliver a particular medical regimen, the System 5 has no authority to prevent such delivery. However, because of the cattleman's lack of training or certification, introduction of medical delivery information derived from the activities of an untrained cattleman into the body of data produced by the present invention may have a diminishing effect on the otherwise robust data body. In such a situation, the System 5 would simply not record data relating to medicines delivered by an improperly trained or certified cattleman. Furthermore, it will be understood and appreciated that other discriminators, above and beyond the identity and training of a particular cattleman, may be used to determine whether or not information relating to an instant medical delivery is to be introduced into the body of data.

If the cattleman 10 is authorized to use the System 5 and, additionally, meets any other criteria or discriminators put in place by the system administrator, the system is primed by application of electrical power to necessary subsystems and components, such as those in the injection arena 30.

Figure 2:
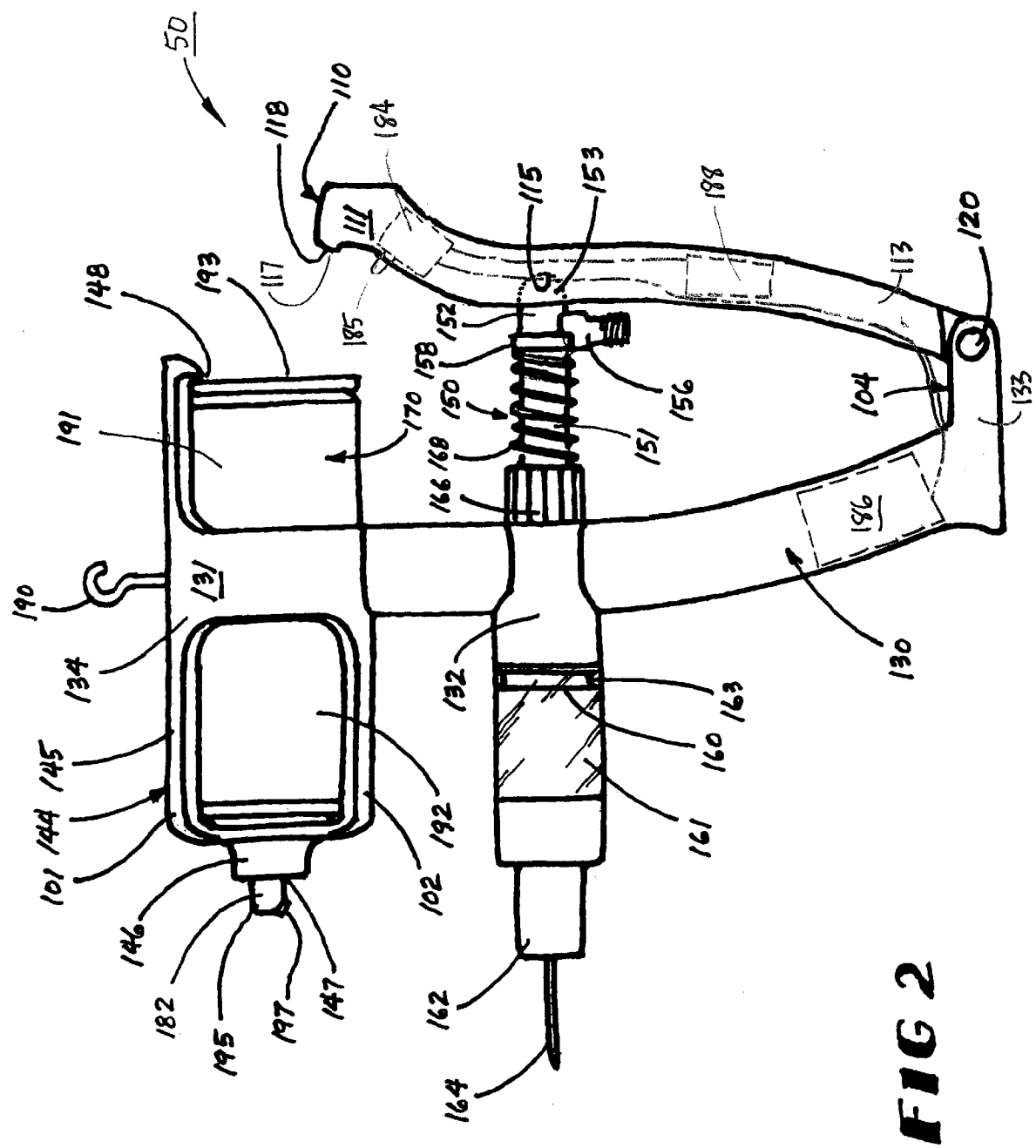
FIG. 2 depicts an exemplary embodiment of a transmitting syringe in accordance with an exemplary embodiment of the present invention.

In preparation for an injection session, the cattleman 10 accesses and prepares for use a syringe such as a transmitting syringe 50. The transmitting syringe 50, described with greater specificity during the later description of FIG. 2, is a syringe having the ability to simultaneously deliver an injection to the animal 40, deliver a marking ink spot to the animal 40, and transmit information relating to the delivery of the injection to a data collector for collection and eventual dissemination.

In a preferred embodiment of the present invention, the transmitting syringe 50 is connected to a medicine reservoir 52 via a medicine conduit 54. It is foreseen that many medical administrations will be of such a small amount, by volume, that the cattleman 10 can retain the medicine reservoir 52 on an arm, leg, or in a backpack-type retention device, for ease of mobility about the injection arena. The medicine conduit 54 is a flexible, tubular member securely interconnected between the transmitting syringe 50 and the medicine reservoir 52. As is well known to those skilled in the administration of medicines to animals, all medicine delivery components must comport with relevant health and safety regulations, especially in view of the highly toxic nature of many such medicines. In preparation for commencement of animal injections, the cattleman 10 may also place a personal data device ("PDD") 56 on his person for recording injection information as will be described momentarily. It will also be understood that the spirit and scope of the present invention specifically contemplates transmitting syringes which, themselves, carry a sufficient amount of medicine to accomplish a desirable number of injections, without requiring either a detached medicine reservoir 52 or a medicine conduit 54.

Now that the System 5 is activated by registration of an authorized user such as the cattleman 10 administering a medical regimen he is authorized to administer, and the necessary medicine delivery components 50, 52 and 54 are in place, an animal 40 is moved into the injection arena 30.

The robustness of the information ultimately derived from the System 5 relies, in significant part, on the reliable linkage between a particular animal such as animal 40 and the injection data derived from delivery of an injection to the animal 40. Toward such end, a reliable animal identification device such as a bolus 45 is attached to the animal 40. As is well known to those familiar with animal identification techniques, the bolus 45 is typically a passive magnetic device which can be deposited in the rumen (stomach) of the animal by swallowing, attached to the ear or other extremity of the animal by an attachment means, or placed under the skin of the animal in an anticipatable location.

Generally, the passive bolus 45 of the present invention emits a detectable electrical signal upon stimulation by a stimulus signal. The electrical signal is unique to the particular animal to which the bolus 45 is attached, and accurate detection of the signal provides an equally accurate identification of the animal.

In an embodiment of the present invention, transmission of a stimulus signal 60 by a stimulus signal transmitter 62 excites the bolus 45 to generate a responsive identification signal 64. A signal receiver 66 is located in sufficient proximity to the animal 40 (optimally within the injection arena 30) so as to detect the identification signal 64. After detection of the identification signal 64, the signal receiver delivers the electrical characteristics of the identification signal 64 to the processor 70 via processor link 68.

As the cattleman 10 delivers the injection to the animal 40 by actuating the transmitting syringe, an ink mark is placed on the animal 40 in close proximity to the location of the injection and, importantly, an injection signal 58 is transmitted from the transmitting syringe 50 to the signal detector 66 for delivery to the processor 70 via processor link 68. After delivery of both an information signal 58 and an identification signal 64 to the processor 70, the information may be linked and transmitted via a communications link 72 to a records database 75.

In another embodiment of the present invention, actuation of the transmitting syringe 50 generates an injection signal 58' to be received by the PDD 56 for short term or temporary storage. The PDD may also, in such an embodiment, be equipped with a signal receiver analogous in functionality to the previously described signal detector 66. In this embodiment, following an injection session, the cattleman 10 may take the PDD 56 back to the personal computer 25 in the farm office 20 and download data relating to particular animals and their respective injections via dataport 26. Following delivery of the downloaded data from the PDD 56 through the dataport 26 to the personal computer 25, the data may be periodically or instantaneously delivered to the processor 70 or a central server for all such devices via a communication link 27.

In yet another embodiment of the present invention, transmission of the stimulus signal 60 by the stimulus signal transmitter 62 may be triggered by a triggering event. In other words, absent a triggering event, no stimulus signal is sent, the bolus is not stimulated to transmit a responsive identification signal 64, and no data relating to a related injection is recorded.

Although many such triggering events are contemplated by various embodiments of the present invention, a representative triggering event is movement of the animal 40 onto a scale 47 or by passing through or otherwise activating a stationary reader designed to detect and monitor the presence of the animal 40 in the desired location. As the animal 40 moves onto the scale 47, the processor 70 controlling the stimulus signal transmitter 62 may allow transmission of the stimulus signal 60. Absent the presence of the animal 40 on the scale 47, no stimulus signal 60 is sent and the animal 40 is not identified. Optionally, the processor 70 may continue to monitor the scale 47 to verify that there is not a significant fluctuation in the weight indicated by the scale. Namely, the processor may be programmed to detect a first animal departing the scale 47 and a second animal moving onto the scale 47, in the event that no injection information was recorded for the first animal. If such a change is detected, the processor simply directs storage of the identification signal elating to the first animal in a segregated data file, followed by transmission of new stimulus signal 60 to detect the identity of the second animal. Such an arrangement further assures parties interested in data integrity that the System 5 was not somehow "sidestepped".

Alternative triggering events can be easily contemplated and fall within the spirit and scope of the preferred embodiments. For example, an infra-red or other similar light beam may be directed across the injection area. The light beam is monitored in much the same way as such a device would be monitored in a home alarm system. When the beam is broken, indicating the presence of the animal, the system is "triggered" into operation. Unexpected "breaks" in expected beam absence may render injection data for that particular injection deletable, as with the unexpected fluctuations in scale readings as referenced above.

In another exemplary embodiment of the present invention, information relating to the identity and injection of an animal 40 may be transmitted directly to a satellite 69 via microwave or other suitable satellite uplink signal 67. The exact source of transmission of the satellite uplink signal 67 is not critical . . . it may originate from a capable transmitter within the transmitting syringe 50, from the PDD 56, or from an intermediate local booster transmitter (not shown), which intermediate local booster transmitter simply takes lower power signals transmitted by the transmitting syringe 50 and/or the PDD 56 and packets the data for transmission by developing appropriate propagation characteristics.

Periodically, the information gathered in accordance with the above specified system is delivered from the processor 70 to a records database 80 for storage and access by authorized users. Control over access to the records database 80 is maintained by a gatekeeper 85. Gatekeepers such as gatekeeper 85 are well known in the data management industry and simply require an individual desiring access beyond the gatekeeper to provide a key, PIN, code word, or other information so that passage beyond the gatekeeper can be limited to those authorized such passage.

In one embodiment, the gatekeeper 85 is linked by a communications link 87 to a subscriber database 90 within a main office 92. The main office 92 may receive information subscription inquiries from parties desiring to be authorized parties, such as breeders 94, pharmaceutical companies 96 and banks 98. If the terms established by principals within the main office 92 are agreeable to such potential authorized parties, and if such potential authorized parties satisfy the agreed upon terms, information specific to the newly authorized party is entered into the subscription database 90. When such newly authorized party, such as a pharmaceutical company 96, for instance, attempts to access the records database 80, the gatekeeper 85 inquires as to the authority of the pharmaceutical company 96 to gain access by checking the subscriber database 90. If the pharmaceutical company 96 is an authorized subscriber, the gateway 85 permits communicative interconnection to the records database 80. Had the pharmaceutical company 96 not been determined to be an authorized user, the gateway 85 would have denied access.

Referring now to FIG. 2, an exemplary embodiment of a transmitting syringe 50 in accordance with an exemplary embodiment of the present invention is shown. More particularly, the transmitting syringe 50 of the preferred embodiment comprises, generally, a syringe handle 104 operatively connected to a transmitting syringe 150 and an ink dispenser 170. The syringe handle 104 comprises a first syringe handle 110 pivotally connected to a second syringe handle 130. The first syringe handle 110 is elongated, having a first end 111 and a second end 113. An ink dispenser interface 117 is located generally adjacent to the socket 115 on the handle 110. The handle 110 has a pivot hole in its second end 113.

The second syringe handle 130 of the transmitting syringe 50 is also elongated and has a first end 131 and a second end 133. The first end 131 of the second syringe handle 130 may securely receive a hook 190 for storage of the marking syringe 105 between uses. The second syringe handle 130 is configured to function as a finger grip for the user. The second end 133 of the second syringe handle 130 is sized to slidably straddle the second end 113 of the first handle 110 and has a pivot hole through its thickness. The second handle 130 includes an integral transmitting syringe collar 132 and an integral ink dispenser collar 134.

During assembly, the second end 133 of the second syringe handle 130 is positioned over the second end 113 of the first syringe handle 110 such that the pivot holes in the ends 113, 133 are axially aligned. Thereafter, a pivot pin 120 is inserted through the aligned holes and appropriately secured therein in any number of ways, including deforming distal ends of the pivot pin 120 so that the diameter of the pivot pin 120 is larger at the points of deformation than the diameter of the pivot pin receiving holes, thereby preventing withdrawal of the pivot pin 120 through the pivot receiving holes. After the pivot pin 120 is properly positioned and secured, the second syringe handle 130 rotates about the axis of the pivot pin 120 in a plane defined by the second syringe handle 130 and the first syringe handle 110. In use, the first and second handles 110, 130 are initially in a spread position. The user can then grip the first and second handles 110, 130 and squeeze them into a closed position as the handles 110, 130 pivot about the pin 120.

The transmitting syringe 150 is mounted between the handles 110, 130 by means of the collar 132 on the second syringe handle 130 and the socket 115 on the first syringe handle 110. The transmitting syringe 150 comprises a transmitting syringe head 152 with a ball 153, an extendible transmitting syringe shaft 151, a transmitting syringe biasing spring 168, a transmitting syringe plunger 160, a transmitting syringe dosage chamber 161, a transmitting syringe needle fastener 162, and a needle 164. In order to connect the syringe 150 to the handle 104, the dosage chamber 161 is threaded into the handle collar 132 of the handle 130, and the transmitting syringe head 152 is connected to the handle 110 by engaging the ball 153 of the head 152 into the socket 115 of the handle 110 in a well known manner.

The head 152 is hollow and further comprises a transmitting syringe nipple 156 and a transmitting syringe stop flange 158. The transmitting syringe nipple 156 may be integral to the hollow transmitting syringe head 152 and is sized to securely receive a syringe vaccine hose (not shown). Vaccine is delivered to the hollow interior cavity of the head 152 via the vaccine hose which is connected to a vaccine source (not shown). The transmitting syringe stop flange 158 extends laterally about the periphery of the transmitting syringe head 152.

The extendible transmitting syringe shaft 151 interconnects the syringe head 152 and the plunger 160. The shaft 151 has an interior axial conduit (not shown) which communicates at one end with the interior cavity of the head 152 and at the other end with an interior axial conduit (not shown) through the plunger 160. The syringe shaft 151 extends through a transmitting syringe collar 132 of the second syringe handle 130 and into the vaccine dosage chamber 161. In order to vary the amount of the dosage, the shaft 151 has a vaccine dosage adjust valve 166. The dosage adjust valve 166 comprises a collar that engages the plunger 160 on one end and is threaded onto the syringe shaft 151.

The transmitting syringe plunger 160 slides within the vaccine dosage chamber 161. An o-ring 163 creates a liquid tight seal between the periphery of the plunger 160 and the interior wall of the dosage chamber 161. The plunger 160 has a check valve (not shown) within its interior axial conduit that allows liquid to pass only in the direction toward the needle end of the syringe 150.

The vaccine dosage chamber 161 is formed of a translucent or transparent material and is secured at its first end to the transmitting syringe collar 132. The vaccine dosage chamber 161 may be scored with incremental graduations to assist a user in dosage measurements. At its second end, the vaccine dosage chamber 161 removably receives a transmitting syringe needle fastener 162. The transmitting syringe needle fastener 162 is fitted to capture a needle 164. A check valve (not shown) is fitted within the needle fastener 162 to allow liquid flow only out of the needle 164.

A transmitting syringe biasing spring 168 is disposed around the transmitting syringe shaft 151 between the transmitting syringe stop flange 158 and the vaccine dosage adjust valve 166. The biasing spring 168 is a compression spring which serves to return the syringe handles 110, 130 to their initial spread position after being squeezed closed by the user.

When the handles 110, 130 are squeezed together, the plunger 160 moves within the dosage chamber 161. The movement of the plunger 160 closes the check valve within the plunger 160 to force vaccine in the dosage chamber 161 through the check valve within the needle fastener 162 and out through the needle 164. When the handles 110, 130 are released by the user, the check valve within the needle fastener 162 closes to preclude fluid or air being drawn into the dosage chamber 161 through the needle 164. Simultaneously, the check valve within the plunger 160 opens to that vaccine is drawn into the dosage chamber 161 through the nipple 156, the hollow head 152, the conduit within the shaft 151, and the conduit within the plunger 160. By turning the dosage adjust valve 166, the length of the shaft 151 is changed. Changing the length of the shaft 151 changes the length of the plunger stroke, and the amount of medicine delivered through the needle 164 is correspondingly changed.

The ink dispenser 170 comprises a self contained storage unit 189. The self contained storage unit 189 may take any number of forms well known to those skilled in the art of marking substance apparatus, including, but not limited to, a canister, a jar, a tube, or the like. Further, the specific form of self contained storage unit 189 is dependent upon the type of ink being utilized. For instance, a pressurized canister maybe used to store ink which is suspended in, or in the form of, a compressed gas. Alternatively, a structure such as that used to store household caulk may be used to store liquid ink.

To support and retain the self contained storage unit 189, the second handle 130 may further comprise an integral retention cage 144 extending from the ink dispenser collar 134. The retention cage 144 may take any number of forms well known to those skilled in the art of mechanical design. It will be appreciated that the form of the retention cage 144 is dependent upon the physical characteristics of the self contained storage unit 189 being used.

The self contained storage unit 189 may comprise a pressurized canister 191, the ink dispenser interface 117 having a contact point 118, a retention cage 144 having a body 145, a valve actuator 146, a tip opening 147, and a can detent 148. The pressurized canister 191 may contain ink in the form of an aerosol, a non-aerosol compressed gas, or the like. The pressurized canister may be mounted to the second handle 130 my means of the collar 134 and the retention cage 144. The pressurized canister 191 comprises a canister body 192 having a bottom surface 193, a valve trigger (not shown), and an ink discharge orifice 182. In order to install the pressurized canister 191 into the handle 104, the canister body is inserted into the handle collar 134 of the second syringe handle 130 and maneuvered into the retention cage 144 until the can detent 148 makes contact with the bottom surface 193 of the canister 191, thereby securely capturing the pressurized canister 191 within the retention cage 144.

After secure capture of the pressurized canister 191 within the retention cage 144, the ink discharge orifice 182 extends through the tip opening 147, and the valve trigger is positioned in contact with, or adjacent to, the valve actuator 146. When fully inserted, the retention cage 144 assures that the bottom of the pressurized canister 191 is aligned with the radial path of rotation of the ink dispenser contact point 118 on the second syringe handle 130, as defined by rotation of the second handle 130 about the pin 120.

Central to the preferred functionality of the transmitting syringe 50 is the transmitter circuitry integral to the transmitting syringe 50. In an exemplary embodiment, the transmitter circuitry comprises a transmit trigger 184, a transmitter 186, and a power source 188. As depicted in FIG. 2, the transmit trigger 184 may be positioned within the handle 110 proximal to the ink dispenser contact point 117. The transmit trigger 184 supports a transmit sensor 185 positioned such that actuation of the transmitting syringe 50 by squeezing handles 110, 130 places the transmit sensor 185 in contact with the pressurized canister 19 1. The transmit trigger, powered by a power source 188 such as a battery, detects contact between the transmit sensor 185 and the pressurized canister 191 and relays an appropriate signal to the transmitter 186. As previously described with reference to FIG. 1, the specific characteristics of the transmitter 186 will vary depending on the particular embodiment of the present invention being practiced, but in all cases, the transmitter is of sufficient signal strength and signal complexity to transmit, at a minimum, the injection event to a receiver.

Optionally, the transmitting syringe 50 may include a flow meter in communication with the transmitting syringe 150 for detecting the amount of medicine delivered in any given actuation. In such an optional embodiment, the transmitter 150 must be of a type to be able to transmit such data to a designated receiver. Similarly, it is within the spirit and scope of the present invention that the transmitting syringe 150 is capable of transmitting and facilitating the recording of the time and date on which medical treatments were given, as well as specifics of the particular treatment, such as the manufacturer of the medicine, the batch number and the date of manufacture.

Figure 3:
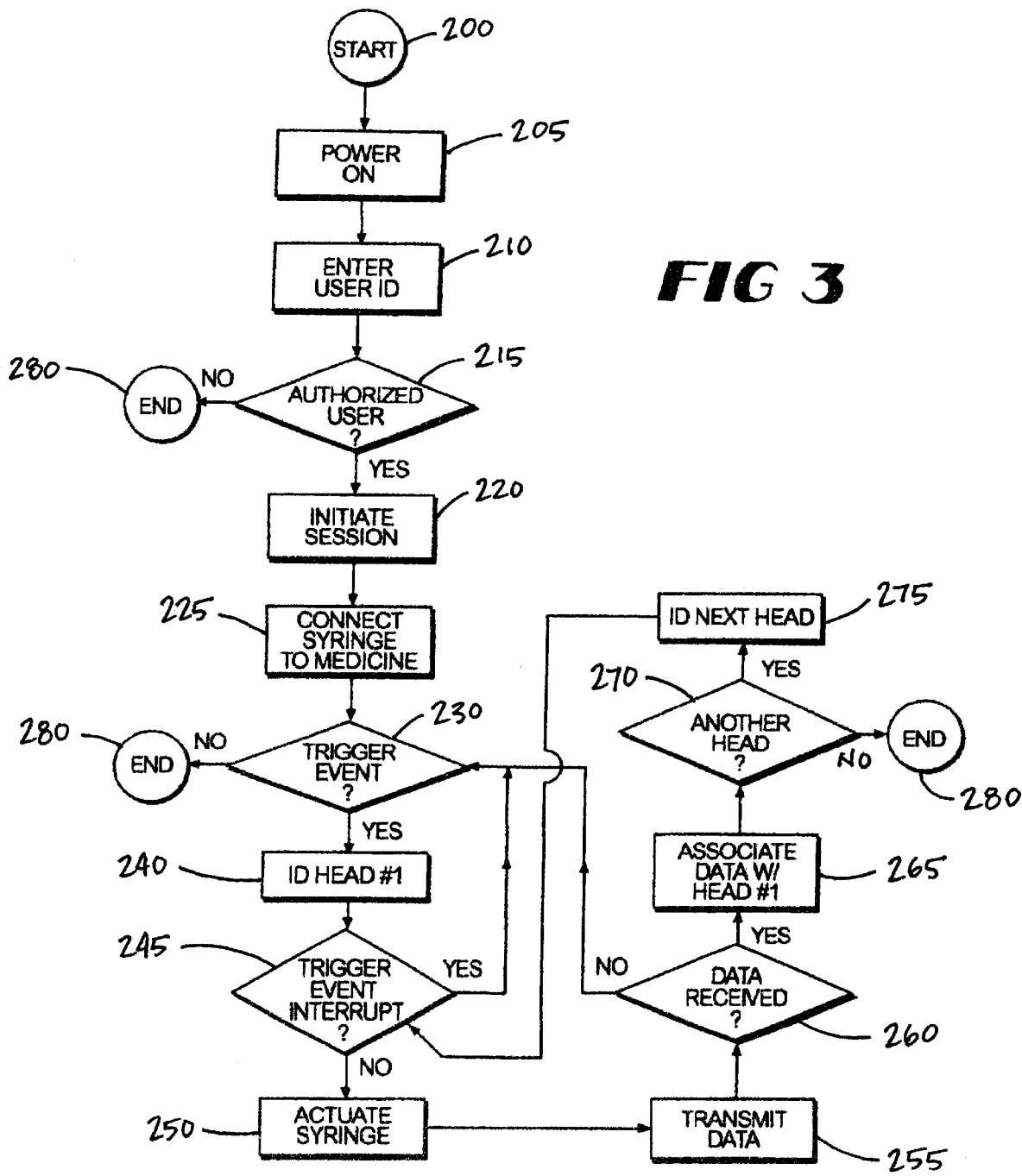
FIG. 3 is a flow diagram detailing exemplary steps in performing the method of the present invention.

Turning now to FIG. 3, a flow diagram detailing exemplary steps in performing the method of the present invention is shown. The method begins at step 200 and, at step 205 the system is "powered on" by a cattleman 10, another operator, or remote device. After being powered on, the system 5 requests input of a user ID at step 210. As previously described, the user ID may be input via PC 25.

At decision block 215, a comparison is done between the user ID entered at step 210 and a list of authorized users maintained in a database such as access database 28. If the user ID entered does not correspond to a user ID maintained in the access database 28, the method of the present invention ends at step 280. If, on the other hand, the user is deemed to be an authorized user, an injection session begins at step 220. Depending on specific system configuration and requirements, session initiation such as that referenced in step 220 may include turning on the trigger device such as scale 47 and waiting for an appropriate trigger signal, as previously discussed. Additionally, before animals may be injected in accordance with the method of the present invention, a syringe 50 must be connected to a medicine reservoir 52 as shown in step 225.

After the set-up steps are complete, the system remains in a "standby" state anticipating a trigger event. If, after a predetermined, prolonged period of time, no trigger event has occurred, the method ends at step 280, per decision block 230. If a trigger event does occur, the head of cattle causing the trigger event is identified in accordance with the particular capabilities of the system of the present invention at step 240.

If, after occurrence of a trigger event but before transmission of data, the trigger event is interrupted (step 245), the method returns to step 230 and awaits another trigger event. If there is no trigger event interrupt, the cattleman actuates the transmitting syringe 50 and delivers the desired injection at step 250. Data relating to the injection is transmitted from the transmitting syringe 50 in step 255 and, at decision block 260, a determination is made as to whether the data was received by the receiver 66. If no data was received, the method of the present invention returns to step 230 and awaits a trigger event. If the data is received, the data is associated with the specific identity of the animal 40 which caused the trigger event and resulting trigger signal at step 265. Thereafter, the present invention awaits the arrival of another head. If, as depicted in decision block 270, another head is detected, that head is identified at step 275, then the method returns to step 245. If, after a predetermined, prolonged period of time, no additional animals are detected, the method ends at step 280.

It will be understood and appreciated that the spirit and scope of the present invention is not limited to the particular embodiments referenced and discussed herein, but to the claims appended hereto.

I claim:

1. A system for automatic recordation of information relating to administration of medicines to animals, comprising:

a transmitting syringe for simultaneously injecting an animal and transmitting, responsive to actuation of the transmitting syringe, a first signal containing information relating to the actuation of the transmitting syringe and the resulting injection of the animal;

an EID, attached to the animal, for providing an electronic identification of the animal;

a receiver for receiving the first signal from the transmitting syringe and the electronic identification of the animal; and a computer database for maintaining the first signal and the electronic identification.

2. The system of claim 1, whereby the transmitting syringe transmits information relating to the amount of medicine injected.

3. The system of claim 1, whereby the EID is an active device.

4. The system of claim 1, whereby the EID is a passive device.

5. The system of claim 4, whereby, responsive to an EID stimulus signal, the electronic identification of the animal is provided.

6. The system of claim 5, whereby the EID stimulus signal is generated by the transmitting syringe.

7. The system of claim 5, whereby the EID stimulus signal is generated by a stimulus signal transmitter.

8. The system of claim 7, whereby the EID stimulus signal transmitter is triggered to transmit the stimulus signal by a trigger event.

9. A method for automatically recording information relating to the administration of medicines to animals, comprising the steps of:

positioning a transmitting syringe in sufficient proximity to an animal so as to effect injection of a medicine from within the transmitting syringe into the animal;

actuating the transmitting syringe to inject the medicine into the animal;

responsive to actuating the transmitting syringe, the transmitting syringe transmitting a first signal;

responsive to a triggering event, an EID attached to the animal providing an electronic identification of the animal; and receiving the first signal and the electronic identification by a receiver.

10. The method of claim 9, comprising the further step of automatically storing the first signal and the electronic identification received by the receiver in a computer database.

* * * * *